(12) United States Patent
Puri et al.

(10) Patent No.: US 7,378,268 B2
(45) Date of Patent: May 27, 2008

(54) ENDOPHYTIC CAMPTOTHECIN AND CAMPTOTHECINOID PRODUCING FUNGI AND PROCESS OF PRODUCING THE SAME

(75) Inventors: Satish Chander Puri, Jammu (IN); Vijeshwar Verma, Jammu (IN); Touseef Amna, Jammu (IN); Geeta Handa, Jammu (IN); Vinay Gupta, Jammu-Tawi (IN); Neelam Verma, Jammu (IN); Ravi Kant Khajuria, Jammu (IN); Ajit Kumar Saxena, Jammu (IN); Ghulam Nabi Qazi, Jammu (IN); Michael Spiteller, University of Dortmund (DE)

(73) Assignee: Council Of Scientific & Industrial Research, New Delhi (IN)

( * ) Notice: Subject to any disclaimer, the term of this patent is extended or adjusted under 35 U.S.C. 154(b) by 352 days.

(21) Appl. No.: 11/020,075

(22) Filed: Dec. 21, 2004

(65) Prior Publication Data

US 2006/0134762 A1    Jun. 22, 2006

(51) Int. Cl.
*C12N 1/14*  (2006.01)
*C12N 1/00*  (2006.01)
*C12P 17/00* (2006.01)
*C12P 17/14* (2006.01)
*C12P 17/16* (2006.01)

(52) U.S. Cl. .................. 435/254.1; 435/117; 435/118; 435/119; 435/120

(58) Field of Classification Search .................. 435/41, 435/245.1, 261, 254.1, 117, 118, 119, 120
See application file for complete search history.

(56) References Cited

U.S. PATENT DOCUMENTS

| | | | |
|---|---|---|---|
| 6,180,855 B1 * | 1/2001 | Hiruma et al. | 800/320 |
| 6,329,193 B1 * | 12/2001 | Strobel et al. | 435/254.1 |
| 6,893,668 B2 * | 5/2005 | Srivastava et al. | 424/779 |

OTHER PUBLICATIONS

Liu Ji-Hua et al. "Isolation of endophytic fungi from *Camptotheca acuminate* and the screening method of antitumor secondary metabolite produced by the fungi". Journal of Plant Resources and Environment. Oct. 2004, vol. 13, No. 4, pp. 6-10.*

Puri et al. "An endophytic fungus from *Nothapodytes foetida* that produces camptothecin". Journal of Natural Products. 2005. vol. 68, No. 12, pp. 1717-1719.*

* cited by examiner

*Primary Examiner*—Vera Afremova
(74) *Attorney, Agent, or Firm*—John P. White; Cooper & Dunham LLP

(57) ABSTRACT

The present invention relates to a novel source of microorganism for production of Camptothecin and related camptothecinoids. The invention also discloses its isolation, screening for Camptothecin production, growth, fermentation requirements and chemical analysis of Camptothecin (camptothecinoids).

12 Claims, 3 Drawing Sheets

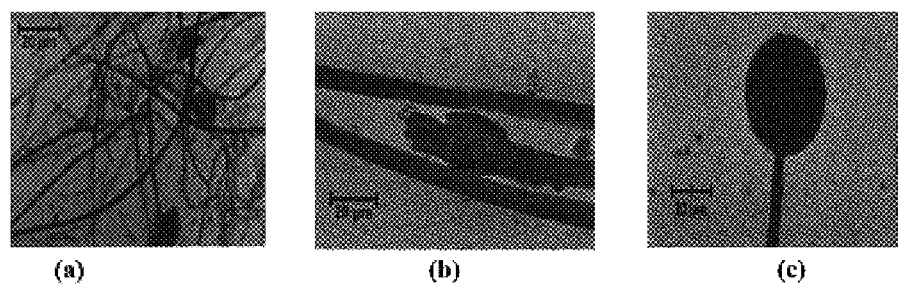
Fig. 1 : (a) Microscopic view of horizontally growing unbranched stoloniferous hyphae (Mag. x 500); (b) Microscopic view of horizontally growing unbranched stoloniferous hyphae (Mag. x 1,000); (c) Microscopic view of the young sporangium of endophytic fungus (Mag. x 1,000)

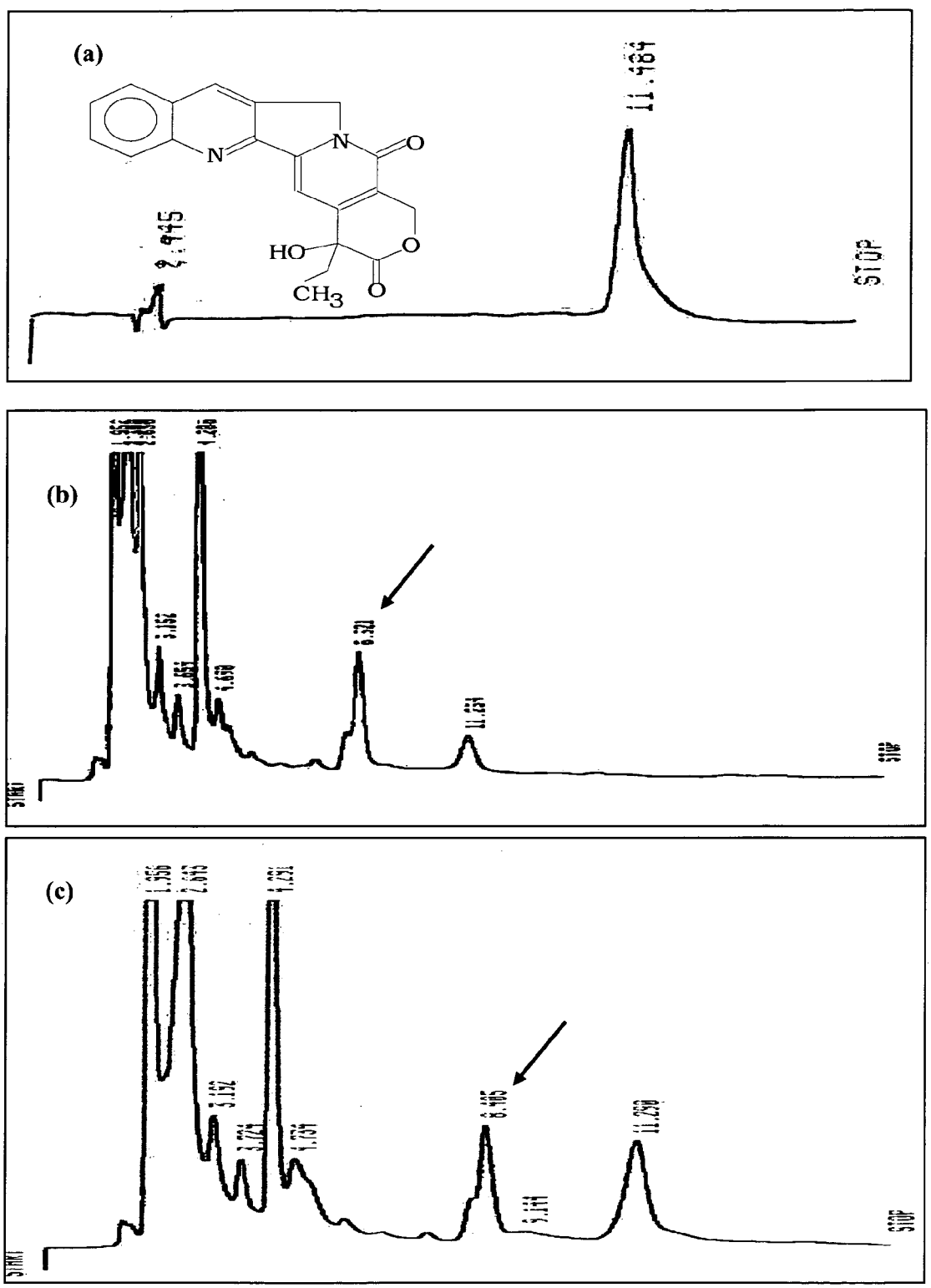
Fig.2: HPLC profile of (a) Authentic Camptothecin (b) Fungal Camptothecin and (c) Cospiked of a&b

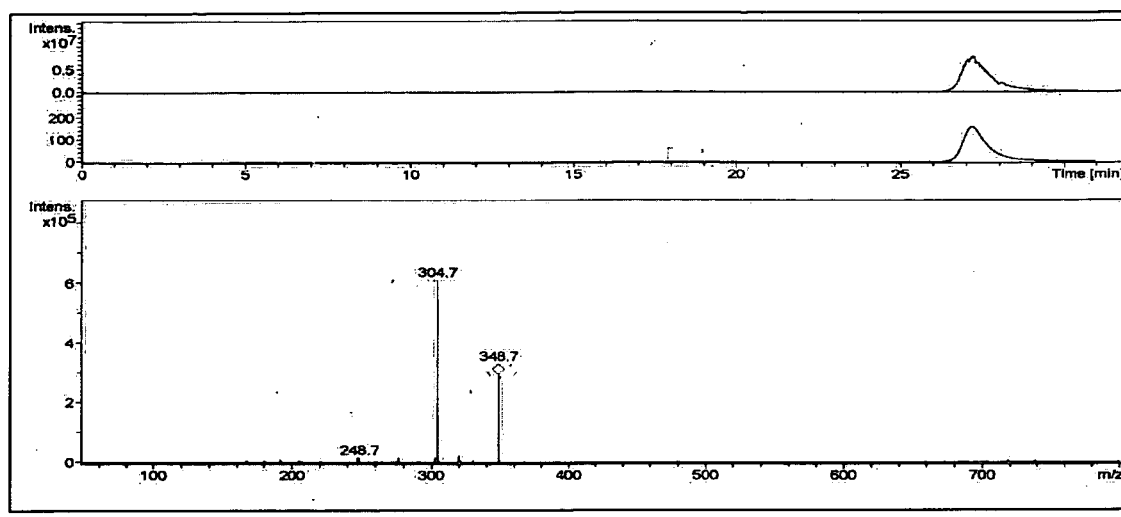
Fig.3: (a) LC/MS profile of Authentic
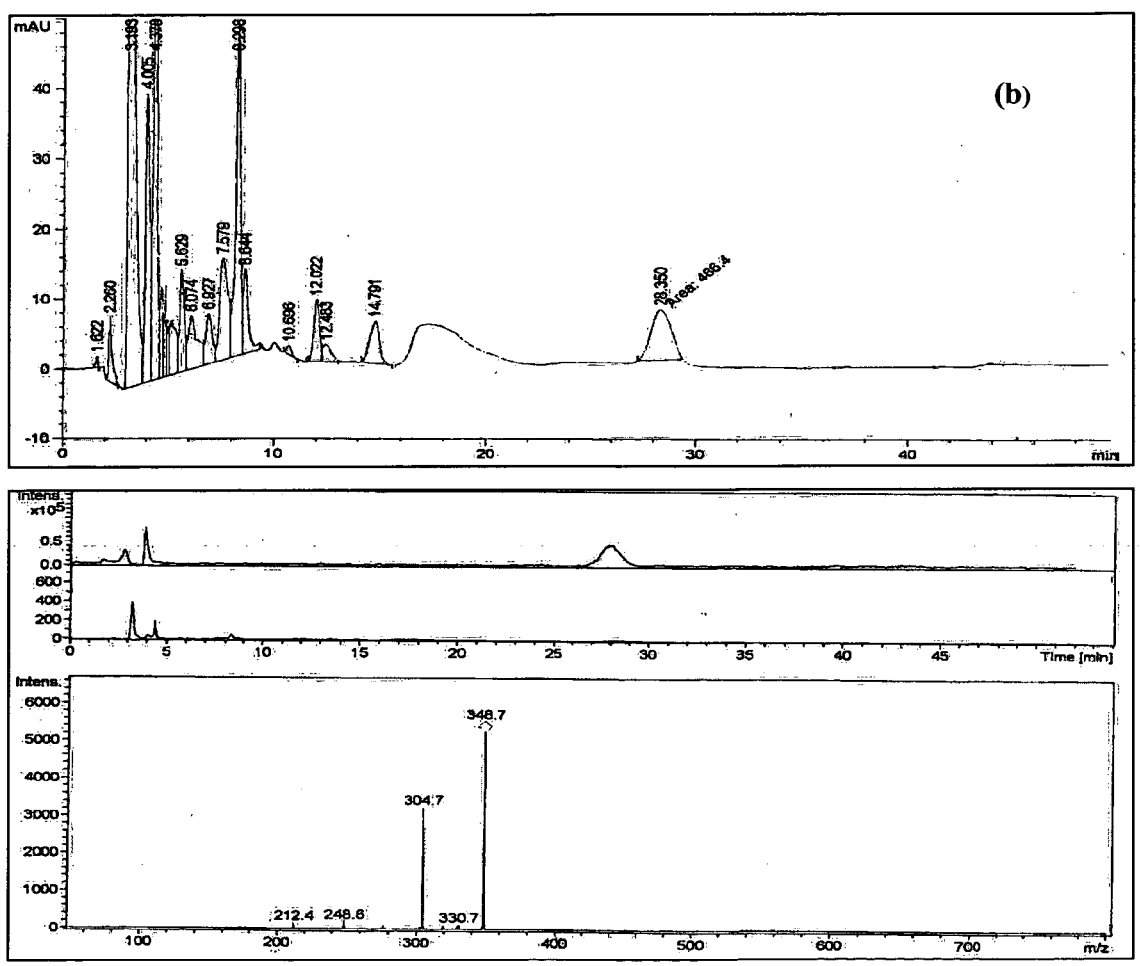
Fig.3: (b) Fungal Camptothecin

ENDOPHYTIC CAMPTOTHECIN AND CAMPTOTHECINOID PRODUCING FUNGI AND PROCESS OF PRODUCING THE SAME

FIELD OF INVENTION

The present invention relates to a novel source of microorganism for production of Camptothecin and related camptothecinoids. The invention also discloses its isolation, screening for Camptothecin production, growth, fermentation requirements and chemical analysis of Camptothecin (camptothecinoids).

BACKGROUND INFORMATION

Camptothecin-(CPT), {4-(S)-4-ethyl-4-hydroxy-1-H-pyrano},[3,4,6,7]-indolizino-(1,2b) quinoline-3,14 (4H, 12H) dione} which is of the chemical structural formula (FIG. 1) belongs to a group of anticancer agents with unique mechanism of action of interfering eukaryotic DNA.CPT and minor camptothecinoids have been obtained in high percentage from Indian tree *Nothapodytes foetida* {Govindachari, T. R. Phytochemistry 11 3529, (1972)} and Japanese species of *Nothapodytes obscura, N. obtusifolia, N. piltosporsides, N. tomentosa* and *N. collina* {Zhang X I and Bao Juchen et al CN. 1, 045 266 (CI Co7D39 261 12 Sep. 1990, C: A. 114 1647607v 1991)}. Other sources of camptothecinoids are *Ophiorhiza mungos* Linn (Tafur et al. Llyodia 39.261 1976) *O. plumila* (Katajimia M. et. al. Tenner YuKi Gagobotsi Toronkai Yoshishu 26 493 1997) *Eryatamia heyneana* wall (Gunsekra S. P. et. al. J. Nat. Prod. 42. 475 1979) and *Merriliodendeon megacarpus* Helms (Arisawa M, et al. Planta. med. 430 404 1981).

*Nothapodytes foetida* (syn; *Mappia foetida*) commonly called "Kalagur" is a small tree distributed in western peninsula from Konkan southward i.e. Nilgiris, Anamalis, Pullneys, North Kanara and Konkan ghats. The anticancer agent isolated from this plant displays an unique mechanism of action as it inhibits intra-nuclear enzyme topoisomerase-I, that is required for swivelling and relaxation of DNA during molecular events such as replication and transcription involved in DNA replication.

Clinical trials of several molecules of this class of compound are in progress in different countries such as Irinotecan (CPT-11) and Topotecan (TPT) have been approved for the treatment of metastatic colorectal cancer and refractory ovarian cancer respectively and their clinical pharmacology have been thoroughly discussed in recent review {Plumbo. M. et al. J. Chromatogr. B, 764 (2001) 121}. New potent and water soluble derivatives have been synthesised and are also now in clinical studies. It was established from SAR studies that functionalization at position 7, 9, 10 and even 11 is compatible with increased activity as shown by 9-amino-20-(S)-camptothecin (9-AC), CPT-11, TPT, N-desmetyl-TPT and other amino containing moieties "Exatecan" (DX-8951) (Mitsui, I. et. al, Jpn. J. Cancer Res 86 (1995) 776). Second generation potent drug candidates at the preclinical stage are more active than CPT like lurtotecan (GG211 or G-1147211) piperazinyl derivative with five or six-member ring at position 10 and 11 which exhibits anti-leukaemia and anti-tumour activity (Takimoto. C. H. et al, Biochim. Biophys. Acta, 1400(1998) 107).

The renewable wild source of *Nothapodytes foetida* has experienced a colossal depletion due to rapidly disturbed and altered eco-system. The germination of *Nothapodyte's* seeds is tedious due to compressed dormancy.

Even though CPT has shown remarkable promise as an anti-tumor agent, unfortunately at the present time the supplies of CPT are inadequate when compared to its projected demand. Thus it is essential to understand how, where and when CPT is biosynthesised in the plants and factor that affect its biosynthesis. As it is well known that many factors influence the production of bioactive molecules which not only include various environmental factors such as temperature and moisture level, but the genetic background of the tree itself: Also plants are commonly hosts to a multitude of microbes including parasites, symbionts, endophytes, epiphytes and mycorrhizal fungi. These organisms may also influence the production of secondary plant metabolites such as phytoalexins whose presence can be triggered by elicitors from microbes. Such microbes may also be capable of production of secondary molecules similar to those produced by the plants.

There are other reasons that prompted the present inventors to devise an "in-vitro" system of CPT production. The system can utilises precursors of CPT, an optimised environment and appropriate plant parts where it is synthesised. The results will be an "in-vitro" system for CPT from the most productive aerial tissue portions of indigenous *Nothapodytes*.

However such "in-vitro" synthesis has many limitations. The source of CPT production from the wild sources either from Chinese *Camptotheca accuminata* or *Nothapodytes foetida* is relatively difficult to meet the demand of the parent compound CPT in view of therapeutic applications in anticancer therapy. Presently isolation from the plant sources or synthesis of camptothecinoids involves multi-step procedure and will be uneconomic.

It is therefore, the objective of the present inventors to investigate, identify and isolate a novel organism for the production of CPT. It is also an object of the present invention to use this microbial source and utilise the fermentation and biotechnology capabilities as a novel mode of preparation of such molecules.

In order to meet the gap between demand and supply of these resources and reduce the greater reliance on wild resources, it is not possible to wait for natural regeneration of vegetative biomass. Therefore attempts have been made to find alternative source in shortest possible time for production camptothecinoids.

OBJECTS OF THE INVENTION

The main object of the present invention relates to a novel endophytic fungal strain of the genus *Entrophospora* having accession no. MTCC 5124, deposited under the Budapest Treaty On The International Recognition Of The Deposit Of Microorganisms For The Purposes Of Patent Procedures on Dec. 19, 2003 at the International Depository Authority, Microbial Type Culture Collection & Gene Bank (MTCC) at Institute of Microbial Technology (IMTECH), Sector 39-A, Chandigarh, New Dehli 160 036, India, for production of Camptothecin and Camptothecinioids CPT).

Another object of the present invention relates to a process of producing and isolating Camptothecin and camptothenoids from a novel endophytic fungal strain having accession no. MTCC 5124, deposited at International Depository at Institute of Microbial technology (IMTECH), Chandigarh, New Delhi, for production of Camptothecin and Camptothecinioids (CPT)

Yet another process of the present invention relates to a process of isolating a novel endophytic fungal strain having accession no. MTCC 5124, deposited at International Depository at Institute of Microbial technology (IMTECH), Chandigarh, New Delhi, for production of Camptothecin and Camptothecinioids (CPT).

BRIEF DESCRIPTION OF ACCOMPANYING DRAWINGS/FIGURES

FIG. 1 (*a*) Microscopic view of horizontally growing unbranched stoloniferous hyphae (Mag.×500)
   (*b*) Microscopic view of horizontally growing unbranched stoloniferous hyphae (Mag.×1000)
   (*c*) Microscopic view of the young sporangium of endophytic fungus (Mag.×1000)
FIG. 2 HPLC profile of (*a*) authentic camptothecin; (*b*) Fungal Camptothecin and (*c*) Cospiked of a & b
FIG. 3 (*a*) LC/MS profile of authentic camptothecin
   (*b*) LC/MS profile of fungal camptothecin

SUMMARY OF THE INVENTION

The present provide a new source in form of a novel endophytic fungal strain having accession no. MTCC 5124, deposited at International Depository at Institute of Microbial technology (IMTECH), Chandigarh, New Delhi, for production of Camptothecin and Camptothecinioids (CPT) and an improved process for producing the same. The present investigation has provided a new source and use fungal for the production of CPT. The fungi has been isolated from the inner bark of a specific *Mappia* species belonging to northwestern Himalayan agro-climatic region.

DESCRIPTION OF THE INVENTION

In terrestrial life microbes exist as parasites, saprophytes endophytes, symbionts or mycorrhizae with possible intergeneric exchange of genetic information between them and their hosts or vice versa. It is well documented that few agrobacteria are capable of genetically transforming their host plants via either the Ri or Ti plasmids which results the formation of genetically transformed plant having one or more characteristics of agrobacterium. Phytohormones such as indole acetic acid, gibberllins, cytokinnins or abscissic acid, can be produced in the plant kingdom by one more plant parasitic bacteria or fungi.

Thus, there is no published evidence that CPT could or would be produced by any micro-organism, the present inventors explored the micro-organism option—the rationale being, that CPT (camptothecinoids) may be produced by one or more microbes associated with the *Mappia* tree.

Logically the basis for this concept is that microbes exists which will produce CPT due genetic exchange previously occurred, either between the microbe(s) (as original source of CPT) or *Mappia* (as original source of CPT). The net result would be the most desirable case of possessing one or more microbes which could be placed in fermentors to produce 20(S)-CPT or other camptothecinoids.

The present invention provides a new source and improved process for producing CPT and its congeners, wherein the investigators have identified a novel endophytic fungal strain having accession no. MTCC 5124, deposited at International Depository at Institute of Microbial technology (IMTECH), Chandigarh, New Delhi, for production of Camptothecin and Camptothecinioids (CPT), This fungus is an endophytic fungus having small hyphae which average 2-3 μm in diameter the mycelia are branched, aseptate, ribbon shaped and multinucleate. Sporangiophores are long, unbranched, and wide and terminate into a sporangium oval to round in shape (FIG. 1). This fungus grows rapidly on many common media, covering plates with its mycelium in 7 to 8 days. The said fungi was obtained from the inner bark of a specific *Mappia* species belonging to northwestern Himalayan agro-climatic region.

The fungus was isolated and identified by placing said tissue fragments on agar medium for 2-7 days and isolating the culture—an endophyte from inner stem bark fragments after surface sterilisation of bark fragment with 50-70% ethanol for 1-20 minutes. Thereafter the fungal hyphae from the said agar medium on mycological agar and again placing said fungal hyphae on said mycological agar if necessary, until a culture in pure form is obtained. extracting all three fractions i.e. cytosolic material, residual pellets and supernatant with solvent as described in (F) above, 3-4 times and evaporating the solvent. The further studies involves to test the production of CPT from the fungi using HPLC and LC/MS and MS-MS studies (FIGS. 2 and 3).

The present study also involved the total DNA isolation from the mucelia of the fungus using modified method as described by Vainio et al (1998). Using the MICRO SEQ D2, using fungal sequencing kit ABI (ABI, USA) the large subunit (LSU) r DNA of the fungus was identified. The present invention further provides a class of microbes which have natural (20S)-CPT-producing characteristics, the details of which are described herein and is only a representative of such microbes and may not be restricted to it alone. The endophytic microbes isolated according to the present procedure produces CPT when cultured under fermentation conditions also discussed herein.

Thus invention provides a fungi which has an ability for the production of CPT.

In the present invention the inventors have also provided studies for improved method for producing a bulk pharmaceutical composition, which contains a pharmaceutically effective amount of a CPT composition, combined with one or more pharmaceutically acceptable inert or physiologically active diluents or adjuvant.

Moreover, the present invention includes a novel method for the production of an agent for the treatment of gastric cancer, intestinal, head and neck tumours and bladder carcinoma when CPT and its analogues or in combination with cisplatin, which comprises administering a pharmaceutical composition containing 20(S)-CPT.

The present invention is directed to fungi, which have camptothecinoids producing characteristics especially as described in the present invention irrespective of their sources. Such microbes are those which can produce CPT authenticated by HPLC, LC/MS and LC/MS/MS. Characteristic ions m/z349(M+H$^+$), m/z 305, 275, 249, 248, 220, 219, 206 and 168 were identical with those of the authentic CPT.

Accordingly, the experiments clearly show that the CPT is being synthesised by the microbe in a given medium.

Accordingly, the main embodiment of the present invention relates to a novel endophytic fungal strain having accession no. MTCC 5124, deposited at International Depository at Institute of Microbial technology (IMTECH), Chandigarh, New Delhi, for production of Camptothecin and Camptothecinioids (CPT), said strain has following characteristics:
   (a) fungal strain forms white colony mycelium and turns black during sporulation,
   (b) forms aerial hyphae, which are round to globose and terminal.

Another embodiment of the present invention relates to the fungal strain, wherein the fungal strain has been isolated from bark of tree *Nothapodytes foetida*.

Another embodiment of the present invention relates to fungal strain, wherein said strain produces about 25 μg/mg of CPT.

Another embodiment of the present invention relates to fungal strain, wherein said strain produces about 18 μg/mg of CPT.

Another embodiment of the present invention relates to fungal strain, wherein said strain produces CPT within 6-7 days of culturing.

Still another embodiment of the present invention relates to a process of isolating Camptothecin and Camptothecinioids (CPT) from novel endophytic fungal strain having accession no. MTCC 5124, said process comprising the steps of:

a. incubating the fungal strain on to a carbohydrate medium for about 6-7 days at temperature of 28±2° C. at 220-220 rpm, b. filtering the fungal mycelia through whatman paper under vacuum to obtain the fungal pellet, c. washing the fungal pellet obtained in step (b) with Tris-HCl buffer (pH-6 to 7), d. resuspending the washed fungal pellet in the same buffer in the ratio of 1:4, e. homogenizing and centrifuging the resuspended pellet at 4° C. at 10,000 to 12,000 rpm for 15-30 minutes, f. extracting the supernant of using organic solvents, and g. identifying CPT using conventional means Yet another embodiment of the present invention relates to a carbohydrate medium, wherein carbohydrate medium in step (a) consist of Peptone about 10 g/litre, Dextrose 40 g/l, Agar One more embodiment of the present invention relates to the organic solvents, wherein organic solvents in step (f) are selected consist of chloroform and methanol mixture in the ratio of 4:1.

Another embodiment of the present invention relates to conventional methods, wherein step (g) the conventional method for identifying CPT involves HPLC, LC/MS.

Yet another embodiment of the present invention relates to a process of isolating a novel endophytic fungal strain having accession no. MTCC 5124 from bark of tree *Nothapodytes foetida* for production of Camptothecin and Camptothecinioids (CPT), said process comprising steps of:

a. cutting small stems from tree of *Nothapodytes foetida*, b. disinfecting the stems with ethanol (5-70%), c. removing the outer bark using a sterile blade, d. putting the pieces of inner bark of the stem onto a agar medium e. achieving the growth of endophytic fungus in 2-5 days, f. reculturing the fungus onto a fresh PDA medium for growth and multiplication, and g. identifying the characteristics of the fungal strain.

The present invention thus provides a new source for the production of the CPT. The earlier known sources for the CPT's were highly expensive and time consuming thus being highly uneconomical. The new source identified in the present study is non-obvious to the person skilled in the art as it's the first source of its kind to be identified which produces CPT. Since CPT is in great demand due to his application in medicine as anticancer compound, therefore it is a necessity and imperative to use and identify alternate sources for CPT production, which are cheaper and economically viable. Further, the presently known source i.e. Nothapodytes foetida is highly endangered plant species and has a very fragile ecosystem. As there is a limited resource of this plant therefore a person skilled in the art and the filed of medicine will appreciate and value such invention and study. Although various investigators have looked for the alternate resources for producing CPT but have not been very successful. No doubt tissue culture techniques have been employed in the culturing and multiplying the plants of *Nothapodytes foetida* for CPT production. However, this technique is also very tedious as this plant is highly recalcitrant. Therefore identification of a new source which is non-recalcitrant would be of great benefit.

The detailed description illustrates the invention by way of example, not by way of limitation of the principles of the invention. This description will clearly enable one skilled in the art to make and use the invention and describes several embodiments, adaptations, variations, alternatives and uses of the invention including what we presently believe is the best mode of carrying out the invention.

The following examples are given by the way of illustrations and therefore should not be construed to limit the scope of the present invention.

EXAMPLES

Example-1

The microbe is a novel endophytic fungus (MTTC 5124) associated with inner bark of *Nothapodytes foetida* (Wight). This microbe was obtained from the inner bark of a specific *Mappia* species belonging to north-western Himalayan agro-climatic region but may not restrict to this species alone.

The aerial tissue fragments from a fully grown tree or the seeds thereof of the genus *Nothapodytes foetida* a medicinal plant which grows widely throughout India including in the North-western Himalayan agro climatic region as well as from southern Konkan forests. The medicinal plant's best suited habitat of north-western agro climatic region is commonly found in north-western ghats of India.

This tissue fragments were placed on agar medium for 2-7 days and isolating the culture—an endophyte from inner stem bark fragments after surface sterilisation of bark fragment with 50-70% ethanol for 1-20 minutes.

A fungal culture designated as (MTCC 5124) was isolated from inner bark of *Mappia* tree and grown on peptone dextrose broth (PDA, peptone 10, dextrose 40 $gl^{-1}$, pH 5-6) and incubated at 28±2° C. in an incubator shaker (200-220 rpm) for 6-7 days. The fungus grows into a mass of mycelium and sporulates sparsely during incubation. The mycelial mat along with the spores was filtered through the Whatman filter paper under vacuum till all the broth was removed. The pellet was washed with Tris.HCl (pH 6-7) buffer and resuspended in the same buffer in the ratio of 1:4. The mycelial mat was homogenized in a homogenizer and centrifuged at 4° C., 10,000-12,000 rpm for 15-30 min. The supernatant was extracted with chloroform and methanol (4:1) mixture. To further confirm the presence of CPT on HPLC and was found identical with authentic control. The left over residue from centrifuged sample was also examined for CPT by HPLC and was also found to contain CPT in traces (FIG. 2 *a,b,c*; FIGS. 3*a* and 3*b*). This was further checked with UV inspection chamber when CPT gave blue spots on comparison with one or more camptothecinoids standards such as CPT, 9-methoxycamptothecin and Mappacin. The characteristic ions m/z349(M+H$^+$), m/z 305, 275, 249, 248, 220, 219, 206 and 168 were identical with those of the authentic CPT.

Example-2

Agar blocks having fungus (MTTC 5124) were fixed and dehydrated for transmission and scanning electron microscopy (SEM). The drying procedure caused some shrinkage of biological structures which means they would be slightly larger and the clumps of cells more tightly packed in the living state (FIG. 1).

Example-3

Cultural Characterisation of Fungal Culture

When an agar plug of inoculum of fungal culture was placed in the centre of freshly prepared agar plates enriched with various nutrients, it grows rapidly and reaches the edge of the plate in 4-5 days. Numerous fluffy aerial mycelial were observed on the agar and the fungus sporulated after 6-7 days with blackish grey coloration.

Example-4

A fungal isolate designated as (MTCC 5124) was grown on medium as described in Example 1. The extracted CPT was co-spiked with standard CPT for authentication of the molecule. The extracted CPT and the added authentic CPT appeared together on the chromatogram thereby confirming the presence of CPT in the culture extract.

The TLC studies carried out showed an A band at R$_f$ 0.67-0.70 that showed blue absorbance at 254 nm. was scraped from the plate and eluted with acetonitrile. This band had same FAB mass spectrum as authentic CPT with an molecular ion peak at m/z 348.7 and prominent peaks at m/z 319.6, 304, 291, 289, 276, 248 219 205, 191, 140 and 109.

The UV spectrum of the compound has an absorbance maximum which is identical to authentic CPT.

In addition the Rf values of CPT preparation from fungus was identical to be authentic CPT.

The amount of CPT (6-7 days culture) is estimated up to 18 μg/mg of chloroform extract. The taxonomy and properties of the microbes revealed to be a fungus belonging to family phycomycetes.

The foregoing description of the specific embodiments will so fully reveal the general nature of the invention that other can by applying current knowledge readily modify and\or adapt for various application such embodiments without departing from the generic concept and therefore such adaptations are intended to be comprehended within the meaning and range of equivalents of the disclosed embodiments. It is to be understood that phraseology or terminology employed herein is for the purpose of description only and not of limitation.

We claim:

1. A novel endophytic fungal strain having accession no. MTCC 5124, deposited at International Depository at Institute of Microbial technology (IMTECH), Chandigarh, New Delhi, for production of Camptothecin and Camptothecinioids (CPT), wherein said fungal strain has following characteristics:
   (a) said fungal strain forms white colony mycelia and turns black during sporulation, and
   (b) said fungal strain forms aerial hyphae, which are round to globose and terminal.

2. The fungal strain of claim 1, wherein the fungal strain has been isolated from bark of tree *Nothapodytes foetida*.

3. The fungal strain of claim 1, wherein fungal strain produces about 25 μg/mg of CPT.

4. The fungal strain of claim 3, wherein said strain produces about 18 μg/mg of CPT.

5. The fungal strain of claim 1, wherein said strain produces CPT within 6-7 days of culturing.

6. A process for isolating Camptothecin and/or Camptothecinioids (CPT) from a novel endophytic fungal strain having accession no. MTCC 5124, said process comprising steps of:
   (a) incubating the fungal strain on a carbohydrate medium for about 6-7 days at temperature of 28±2° C. at 220-220 rpm,
   (b) filtering the fungal mycelia through whatman paper under vacuum to obtain a fungal pellet,
   (c) washing the fungal pellet obtained in step (b) with Tris-HCl buffer having a pH of 6 to 7,
   (d) resuspending the washed fungal pellet in the same buffer in the ratio of 1:4,
   (e) homogenizing and centrifuging the resuspended pellet at 4° C. at 10,000 to 12,000 rpm for 15-30 minutes,
   (f) extracting the supernatant using an organic solvent, and
   (g) isolating Camptothecin and/or CPT from the extract obtained in step (f).

7. The process of claim 6, wherein the carbohydrate medium in step (a) comprises Peptone at about 10 g/litre, Dextrose at 40 g/l, and Agar.

8. The process of claim 6, wherein the organic solvent in step (f) is a mixture of chloroform and methanol in the ratio of 4:1.

9. The process of claim 6, wherein the Camptothecin and/or CPT isolated in step (g) is identified by high performance liquid chromatography (HPLC) and/or liquid chromatography/mass spectrometry (LC/MS).

10. The process of claim 6, wherein the fungal strain is isolated from bark of a *Nathapodytes foetida* tree.

11. The process of claim 6, wherein said strain produces about 25 μg/mg of CPT.

12. The process of claim 11, wherein said strain produces about 18 μg/mg of CPT.

* * * * *